(12) United States Patent
Jamello

(10) Patent No.: US 10,387,013 B2
(45) Date of Patent: Aug. 20, 2019

(54) SYSTEMS AND METHODS FOR CONTROLLED SINGLE TOUCH ZOOM

(71) Applicant: ACIST Medical Systems, Inc., Eden Prairie, MN (US)

(72) Inventor: Joseph A. Jamello, Saratoga, CA (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 428 days.

(21) Appl. No.: 14/508,394

(22) Filed: Oct. 7, 2014

(65) Prior Publication Data

US 2015/0099968 A1 Apr. 9, 2015

Related U.S. Application Data

(60) Provisional application No. 61/887,599, filed on Oct. 7, 2013.

(51) Int. Cl.
*G06F 3/0484* (2013.01)
*G06F 3/0488* (2013.01)
*A61B 5/00* (2006.01)
*A61B 8/12* (2006.01)
*A61B 8/00* (2006.01)

(52) U.S. Cl.
CPC ........ *G06F 3/04845* (2013.01); *A61B 5/0066* (2013.01); *A61B 5/743* (2013.01); *A61B 8/12* (2013.01); *A61B 8/465* (2013.01); *A61B 8/467* (2013.01); *G06F 3/04883* (2013.01); *A61B 5/7475* (2013.01); *G06F 2203/04805* (2013.01); *G06F 2203/04806* (2013.01)

(58) Field of Classification Search
CPC .................................................. A61B 5/0066
See application file for complete search history.

(56) References Cited

U.S. PATENT DOCUMENTS

| 7,844,915 B2 | 11/2010 | Platzer et al. | |
|---|---|---|---|
| 2004/0015079 A1* | 1/2004 | Berger | G01S 7/52025 600/437 |
| 2008/0260248 A1* | 10/2008 | Kondo | G06T 3/40 382/173 |
| 2009/0300540 A1* | 12/2009 | Russell | G06F 3/0483 715/783 |

(Continued)

FOREIGN PATENT DOCUMENTS

| CN | 101794192 A | 8/2010 |
|---|---|---|
| CN | 102081495 A | 6/2011 |

(Continued)

OTHER PUBLICATIONS

Bürger, Neal, and Andreas Butz. "Single Touch Zoom Gestures on a Mobile Device"; Ludwig Maximilian University of Munich; Teaching and research unit media computer science; 2010, pp. 1-33.

(Continued)

*Primary Examiner* — Rochelle D Turchen
(74) *Attorney, Agent, or Firm* — Fredrikson & Byron, P.A.

(57) ABSTRACT

Systems and methods are disclosed for performing a zoom operation based on a single motion input. A user interface can be adapted to display an image, detect a single motion input and contemporaneously control a zoom operation on the image. Zoom operations can include a zoom magnitude, direction, and distance. Single motion inputs can include, for example, a swipe of a finger on a touchscreen or a click and drag operation performed on a mouse.

33 Claims, 15 Drawing Sheets

(56) References Cited

U.S. PATENT DOCUMENTS

| | | | |
|---|---|---|---|
| 2010/0031169 A1* | 2/2010 | Jang | G06F 1/1624 715/760 |
| 2010/0179427 A1* | 7/2010 | Yamamoto | A61B 8/00 600/443 |
| 2011/0210922 A1* | 9/2011 | Griffin | G06F 1/1624 345/173 |
| 2014/0270436 A1* | 9/2014 | Dascal | G06T 7/11 382/130 |

FOREIGN PATENT DOCUMENTS

| | | |
|---|---|---|
| CN | 102364428 A | 2/2012 |
| CN | 102985903 A | 3/2013 |
| CN | 103210367 A | 7/2013 |
| CN | 103237503 A | 8/2013 |
| EP | 2128748 A2 | 12/2009 |
| EP | 2191776 A1 | 6/2010 |
| JP | 2007535733 A | 12/2007 |
| WO | 2004107980 A2 | 12/2004 |
| WO | 2011109282 A1 | 9/2011 |
| WO | 2012001625 A1 | 1/2012 |
| WO | 2013148730 A2 | 10/2013 |

OTHER PUBLICATIONS

International Search Report and the Written Opinion of the International Searching Authority, or the Declarations, for co-pending Intl. Pat. App. No. PCT/US2014/059423, dated Dec. 23, 2014, pp. 1-13.

* cited by examiner

SYSTEMS AND METHODS FOR CONTROLLED SINGLE TOUCH ZOOM

CROSS REFERENCES

This application claims the benefit of U.S. Provisional patent application Ser. No. 61/887,599, filed Oct. 7, 2013 the entire contents of which are hereby incorporated by reference.

BACKGROUND

Electronic images are displayed and examined in a variety of contexts. In some circumstances it may be useful to zoom in or out of the image. One such example is intravascular imaging, which is used to identify diagnostically significant characteristics of a vessel.

SUMMARY

This disclosure generally relates to systems and methods that may be used to perform a controlled zoom operation based on a single motion input. In one example, a user interface may be configured to display images and receive inputs from a user. The user interface may include an image display region configured to display an electronic image. The user interface may also be configured to include a zoom function that allows a user to zoom in or out to assist in examining the electronic image. The user interface may also be configured to perform controlled zoom operations based on single motion inputs received from the user. The single motion inputs may comprise an engage input and a motion input (e.g., a swipe on a touch screen, or a click and drag of a mouse). The user interface may determine a zoom magnitude, a zoom type, and a zoom center based on the single motion input. In some examples, the user interface may also be configured to perform translation operations based on a single motion input. In certain examples the user interface may also be configured to perform a toggle operation.

Examples described in this disclosure may provide one or more advantages over existing systems and methods. For example, some of the described systems and methods allow a user to simply perform a controlled zoom operation which includes determining a zoom center, a zoom magnitude, and a zoom type, using only a single motion input like a swipe of a finger. This simplified zooming operation allows for a streamlined zooming experience.

Embodiments of the invention include devices configured to perform such zoom functions, computer-readable media capable of executing instructions to perform such zoom functions, and methods of performing such zoom functions.

The details of one or more examples are set forth in the accompanying drawings and the description below. Other features, objects, and advantages will be apparent from the description and drawings, and from the claims.

BRIEF DESCRIPTION OF DRAWINGS

The following drawings are illustrative of particular examples of the present invention and therefore do not limit the scope of the invention. The drawings are not to scale (unless so stated) and are intended for use in conjunction with the explanations in the following detailed description. Examples of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Embodiments of the invention include a single motion zoom operation useful for examining an electronic image. Although such a controlled zoom function could be useful in a variety of environments and applications, this disclosure will primarily refer to such controlled zoom operations in the context of a user interface for an intravascular imaging system employing intravascular ultrasound (IVUS), optical coherence tomography (OCT), or other suitable imaging techniques used to generate an intravascular image. The disclosed systems and methods may be useful in the medical field where medical equipment often employs user interfaces in a sterile field.

Figure 1:
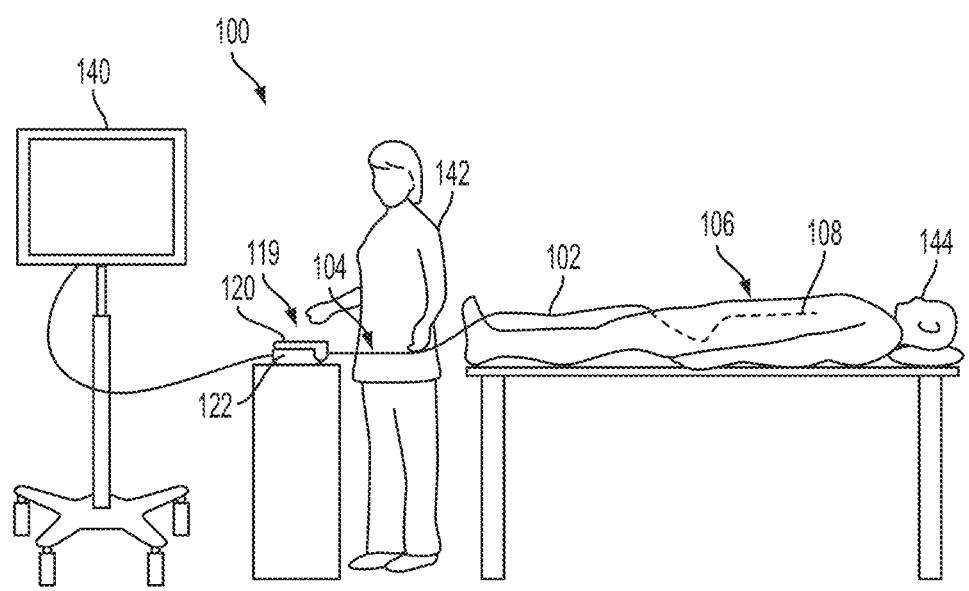
FIG. 1 is an illustrative example of a system configured to perform intravascular imaging.

FIG. 1 is an illustrative example of a system 100 that may be configured to perform intravascular imaging. System 100 may include a catheter assembly 102, a translation device 119, and a computing device 140. The catheter assembly 102 may include a proximal end 104 and a distal end 106 configured to be inserted into a vessel of a patient 144. In one example, catheter assembly 102 may be inserted into the patient 144 via the femoral artery and guided to an area of interest within the patient 144. The broken lines in FIG. 1 represent portions of catheter assembly 102 within the patient 144.

In some examples, catheter assembly 102 may include an intravascular imaging device 108 within distal end 106 configured to emit and receive wave-based energy and generate imaging data—e.g., to image the area of interest within the patient 144. For example, where system 100 is an IVUS system, intravascular imaging device 108 may comprise an IVUS imaging probe including an ultrasound transducer configured to emit and receive ultrasound energy and generate ultrasound data. In another example, system 100 may be an OCT system wherein the intravascular imaging device 108 may comprise an OCT imaging probe configured to emit and receive light and generate OCT data.

The translation device 119 may be configured to translate the intravascular imaging device 108 of the catheter assembly 102. The translation device 119 may comprise a linear translation system (LTS) 122. As is discussed elsewhere herein, LTS 122 may be mechanically engaged with catheter assembly 102 and configured to translate the catheter assembly 102 a controlled distance within the patient 144 during a translation operation, for example a pullback or push-forward operation. System 100 may comprise a patient interface module (PIM) 120 configured to interface the translation device 119 with the catheter assembly 102.

A computing device 140 may be in communication with the intravascular imaging device 108 and the translation device 119. According to some examples, computing device 140 may comprise an imaging engine and a user interface. The imaging engine may include one or more programmable processors and one or more memory modules. One or more programs and/or executable instructions may be stored on the one or more memory modules and be configured to be executed by the one or more processors. The imaging engine may be configured to process imaging data received from the intravascular imaging device 108. In some examples, the imaging engine may comprise one or more programming modules including, but not limited to, an imaging module, an interface module, and a zoom module. The imaging module may be adapted to receive imaging data and generate an electronic image based on the imaging data. The interface module may be adapted to receive user inputs from a user, for example from a mouse or a touchscreen, and display an electronic image to the user. In some examples, the interface module may be adapted to detect a single motion input from a user. In such examples, a zoom module may be adapted to control a zoom operation on the electronic image contemporaneously with detection of the single motion input to cause the interface module to display the electronic image at a different magnification and/or translate the electronic image. Different examples may include other programming modules as suitable for a particular purpose.

In some examples, the computing device 140 may include a user interface configured to receive inputs from a system user 142 and/or display data acquired from the catheter assembly. In some examples, the user interface may be in communication with the imaging engine and be configured to display images rendered by the imaging engine. The user interface may comprise any input/output device suitable for a particular application. For example, a user interface may comprise a touchscreen configured to allow a user to interact with a display using, for example, a fingertip or a stylus. The touch screen may be of any type including, for example, a resistive touchscreen, a surface acoustic wave touchscreen, or a capacitive touchscreen. In some examples, the user interface may comprise computer peripherals (e.g., mouse and keyboard), software (e.g., voice recognition), or any other suitable devices or programs to receive inputs from the user.

Figure 2:
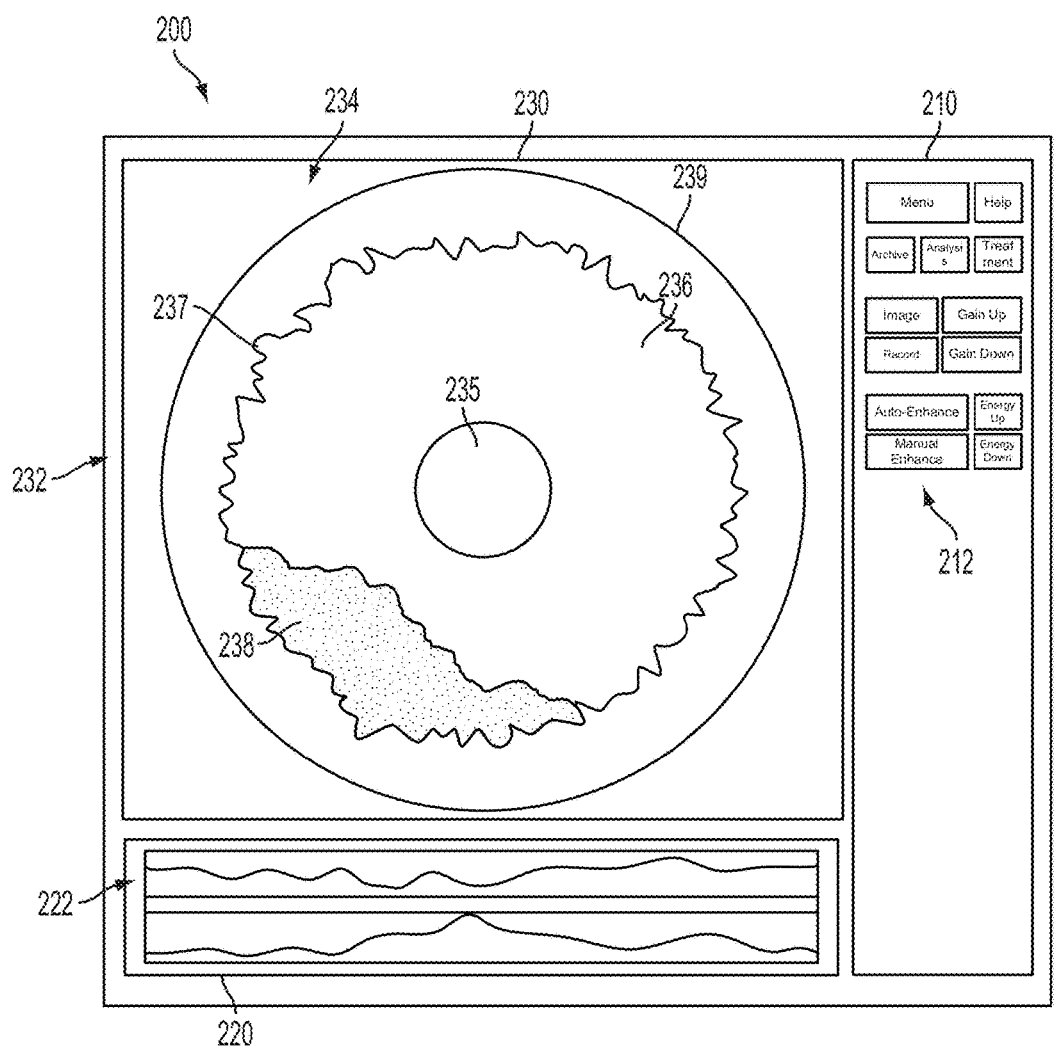
FIG. 2 is an illustrative example of a user interface.

FIG. 2 is an illustrative example of a user interface 200 that may be used in system 100 of FIG. 1. User interface 200 may comprise a menu 210, data display region 220, and an image display region 230. Menu 210 may be configured to receive inputs from the user and may include selectable graphic icons 212 associated with specific functions or tasks performable by user interface 200 or an imaging engine in communication with user interface 200. As noted above, user interface 200 may be configured to display to a user imaging data received from an imaging engine. Imaging data displayed by user interface 200 may be substantially real-time or stored in one or more memory modules of the imaging engine. Image display region 230 and data display region 220 may be configured to display imaging data comprising, for example, an image, such as an intravascular image. The image may include a focal point, such as an area of interest, a reference area, or other feature useful for association with a zoom operation.

In one example, image display region 230 may display an electronic image 232 comprising a short view cross-section 234 of a vessel 239 of a patient. The electronic image 232 may be rendered by an imaging engine with imaging data generated by an intravascular imaging device. In this example, the electronic image 232 includes a focal point of a catheter mask 235 within a vessel lumen 236 of vessel 239 and may be used to help a healthcare professional identify diagnostically significant characteristics of the vessel 239 (e.g., blockages, lesions, location of a stent). For example, electronic image 232 may show a lesion 238 on a vessel wall 237.

In some examples, user interface 200 may also be configured to receive inputs from a user. For example, image display region 230 and data display region 220 may be configured to receive inputs from a user. For example, image display region 230 may display a short view cross-section 234 of vessel 239, while data display region 220 may display a long view cross-section 222 of vessel 239. In some examples, the data display region 220 may be configured to receive a selection from the user indicative of a position within vessel 239 on the long view cross-section 222. Upon receiving the selection, user interface 200 may display the short view cross-section 234 of vessel 239 corresponding to the selected position within the vessel selected by the user on the long view cross-section 222. Such examples provide the diagnostic benefits as a user is able to survey vessel 239 of a patient using the long view cross-section 222 and quickly access a more detailed short view cross-section 234 of vessel 239.

In some examples, user interface 200 may be configured to provide a zoom function. A zoom function may provide certain diagnostic benefits by allowing a user to more closely inspect a specific area of interest. For example, a zoom function of user interface 200 may be used to zoom in on the short view cross-section 234 to more closely examine lesion 238 of vessel 239.

In some examples, user interface 200 may be configured to control a zoom operation based on a single motion input from a user (e.g., comprising, consisting, or consisting essentially of a single motion input). User interface 200 may be configured to perform a zoom operation by determining one or more of a zoom magnitude, a zoom type, and/or a zoom center based on the single motion input. A single motion input may comprise a single engage followed by a drag motion (e.g., a single drag motion to a disengage point). In one example, a single motion input may be performed on a touchscreen by touching the touchscreen with a fingertip or stylus and dragging the fingertip or stylus along the surface of the touchscreen. In another example, a single motion input may be performed by a mouse by holding down a mouse button and dragging the mouse.

The user interface may be configured to detect a single motion input from a user and control a zoom operation based on the single motion input. In some embodiments, the user interface includes a context area, a boundary, and a boundary point. The context area can be a defined area within the boundary of the user interface useful for performing zoom operations. The boundary can be a known perimeter of the user interface and can generally coincide with an underlying electronic image. The boundary point can be any point along the boundary. In some embodiments, the imaging engine is configured to automatically identify the focal point of the electronic image and overlay the context area with the focal point. In other embodiments, the imaging engine is configured to receive an input from a user to overlay the context area with the focal point of the electronic image.

Figure 3A:
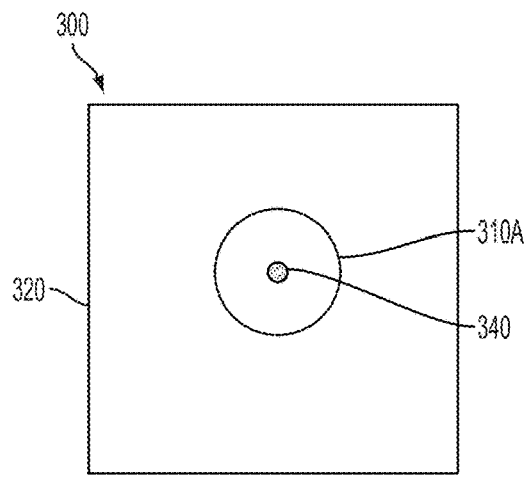
FIGS. 3A-3F are illustrative examples of an image display region of a user interface.
Figure 3B:
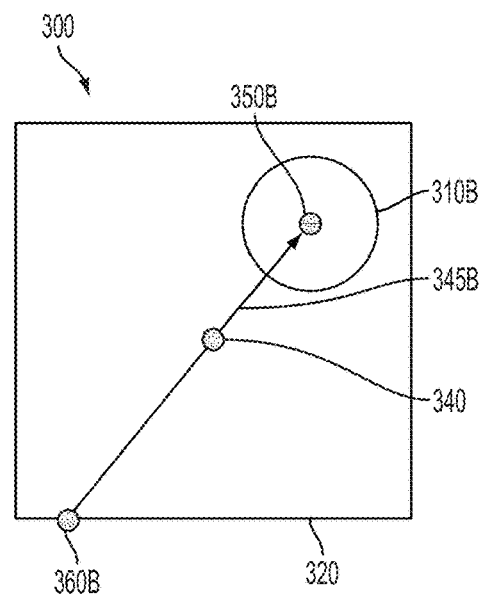
Figure 3C:
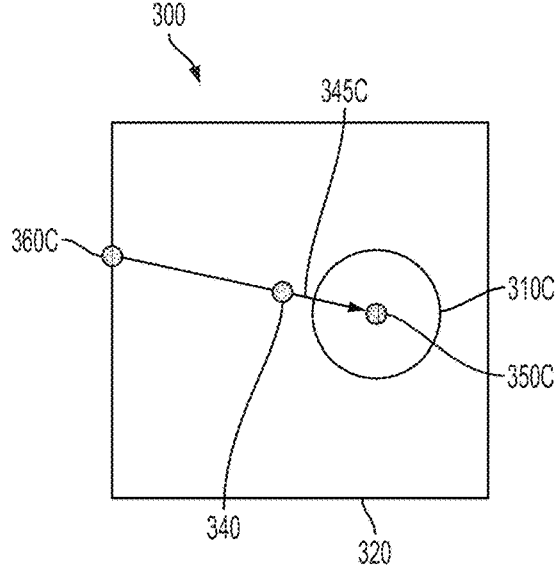

FIGS. 3A-3C are illustrative examples of an image display region 300 of a user interface. The user interface may be configured to detect a single motion input from a user and control a zoom operation based on the single motion input. In this example, image display region 300 includes a context area 310, a boundary 320, and a boundary point 360. This example also includes a single motion input comprising an engage point 340 beginning within the context area 310 and a drag point 350 extending towards the boundary 320. The sequence of FIGS. 3A-3C chronologically illustrates a method for receiving a single motion input.

FIG. 3A illustrates image display region 300 including the context area 310A within the boundary 320. In this example, the image display region 300 has detected an engage point 340 within the context area 310A. The engage point 340 may be representative of an input on a touchscreen from a fingertip or stylus, or a pressing of a mouse button.

FIG. 3B shows image display region 300 after a drag motion has been performed. In this example, the input has been dragged from engage point 340 to drag point 350B. As shown in FIG. 3B, the single motion input adjusts the location of the context area 310B with respect to boundary 320. Boundary point 360B may be a point on boundary 320 that is aligned with engage point 340 and drag point 350B. In some examples, boundary point 360B may be the point on the boundary 320 such that engage point 340 is between boundary point 360B and drag point 350.

In some examples, a zoom magnitude may be correlated with a distance between boundary point 360B and drag point 350B, or between engage point 340 and drag point 350B. For example, a zoom magnitude may be equal to the quotient between a distance between the drag point 350B and the boundary point 360B and the distance between the engage point 340 and the boundary point. In certain examples, the maximum limit is equal to 2× and the zoom magnitude may be any value between 1× and 2×. Thus, the zoom magnitude may be infinitely variable between 1× and 2× as there are an infinite number of points between engage point 340 and boundary 320 on which drag point 350B may be positioned.

In some examples, it may be desirable to have magnification greater than or less than 2×. In such examples, a magnification limit, representative of a maximum magnification, may be used to determine the zoom magnification. For example, a zoom magnitude may be determined by multiplying the magnification limit by the quotient of the distance between drag point 350B and engage point 340 and the distance between engage point 340 and boundary point 360B. In such examples, the zoom magnitude may be infinitely variable between 1× and the magnification limit. In some examples, the magnification limit may be manually set by a user. In certain examples, an imaging engine may be configured to automatically determine the magnification limit based on characteristics of an electronic image. Representative embodiments of magnification limits include any limit within the range of 1.5× to 10×.

FIG. 3C shows image display region 300 after a drag motion where drag point 350B is moved to drag point 350C. As in FIG. 3B, the continuation of the single motion input adjusts the location of the context area 310 with respect to boundary 320 from context area 310B to context area 310C. As shown in this example, the location of boundary point 360B also moves to align with engage point 340 and drag point 350C, moving from boundary point 360B to boundary point 360C.

In some examples, a zoom type may be determined based on a direction of movement of drag point 350 relative to engage point 340. For example, after engaging, moving the drag point 350 farther away from engage point 340 causes a zoom in operation, whereas moving the drag point 350 closer to engage point 340 causes a zoom out operation. With respect to FIGS. 3A-3C, the single motion input received between FIGS. 3A and 3B causes the drag point 350 to move farther away from engage point 340 and therefore corresponds with a zoom in operation. Conversely, the continuation of the single motion input between FIGS. 3B and 3C causes the drag point 350 to move closer to engage point 340 and therefore corresponds with a zoom out operation.

Any of the zoom operation methods and systems described herein can be performed on a user interface employing a coordinate system. Such an interface is useful for setting known initial positions of the focal point of the image, context area, and boundary, and tracking movements of the context area and/or focal point with respect to the boundary. The coordinate systems of the electronic image and the user interface can be the same or different. In embodiments where they are different, the imaging engine can calculate a translation between the two coordinate systems during movements. In some examples, an imaging engine can be configured to determine a zoom magnitude and an image center by mapping a single motion input into a coordinate system having perpendicular axes. In such examples, based on the coordinates associated with the single motion input, the imaging engine can use a maximum value of the single motion input along either axes to determine a zoom magnitude and a lesser distance of the single motion input along either axes to determine a new image center.

Figure 3D:
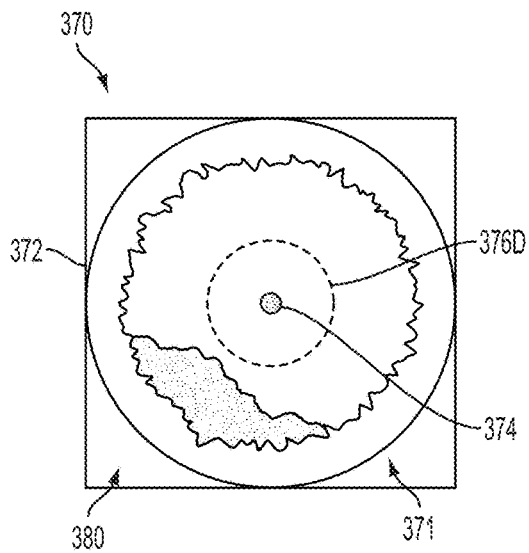
Figure 3E:
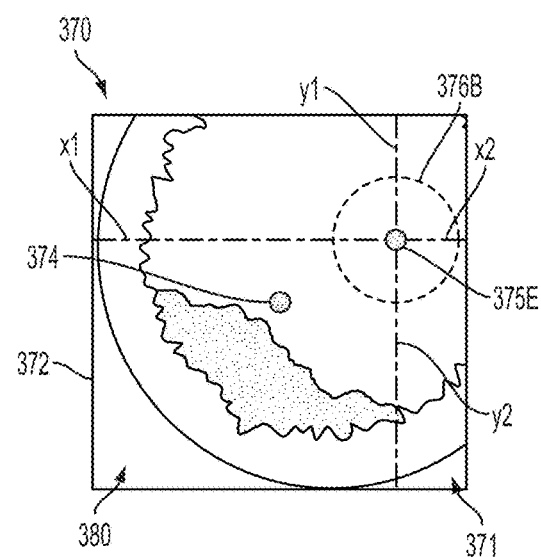
Figure 3F:
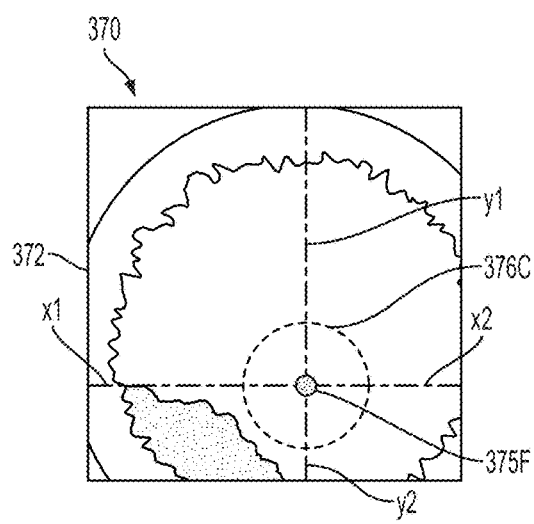

FIGS. 3D-F are illustrative of examples that employ a coordinate system. In these examples, image display region 370 can include a coordinate system 380. As noted above, coordinate system 380 can be used to track user inputs to facilitate control of a zoom operation. In some examples, coordinate system 380 can include a frame of reference. In such examples, a distance between user inputs and the frame of reference can be calculated to determine a zoom magnitude and direction. In some examples, a frame of reference can comprise one or more axes, for example, an x-axis and a y-axis. In this example, coordinate system 380's frame of reference is boundary 372. Thus, in this example, user inputs are tracked based on the distance between the user input and boundary 372. The sequence of FIGS. 3D-3F chronologically illustrate receiving a single motion input beginning within context area 376 and tracking the single motion input relative to boundary 372 of coordinate system 380 to control a zoom operation.

FIG. 3D illustrates the beginning of a user input comprising a drag motion. In this example, a user input is detected at engage point 374 within context area 376D. As noted above, the user input at engage point 374 can be representative of a user input received, for example, from a touch screen or a click of a mouse.

FIG. 3E illustrates the user input extending from engage point 374 to drag point 375E. In some examples, a zoom operation can be controlled using coordinate system 380. More specifically, the zoom magnitude, direction, and distance can be based on the position of drag point 375E relative to coordinate system 380's frame of reference, e.g., boundary 372. In some examples, the zoom magnitude can be correlated with the quotient of a distance between drag point 375E and boundary 372 and a dimension of boundary 372, for example a width or height of boundary 372. As shown in FIG. 3E, the distance between drag point 375E and boundary 372's left side, right side, top side, and bottom side is x1, x2, y1, and y2, respectively. In some examples, the greatest horizontal or vertical distance between drag point 375E and boundary 372 can be used to determine the zoom magnitude. In situations where the greatest horizontal and vertical distances are equal, either value may be used to determine the zoom magnitude. In this example, x1>y2>y1>x2. Thus, x1 is the greatest horizontal or vertical distance and can be used to determine a zoom magnitude. In this example, the zoom magnitude can be determined based on the ratio between xl and the width of boundary 372 (i.e., x1+x2). In some examples, this ratio/quotient and a maximum magnification can be used to determine the zoom magnitude of the zoom operation based on drag point 375E. For example, where the maximum magnification is 2×, a zoom magnitude can be the product of the ratio/quotient and the maximum magnification. As noted above, the zoom direction and distance of the zoom operation can also be based on location of drag point 375E relative to boundary 372. In this example, electronic image 371 is translated and positioned within image display region 370 according to the location of drag point 375E relative to boundary 372. More specifically, electronic image 371 is centered around drag point 375E by translating it horizontally a distance x1 and x2 from the left and right side of boundary 372, respectively, and vertically a distance y1 and y2 from the top and bottom side of boundary 372, respectively. As can be appreciated, in examples where coordinate system 380 includes axes and determines Cartesian coordinates for user inputs, such coordinates can also be used to calculate a zoom magnitude, direction, and distance.

FIG. 3F illustrates the user input extending to drag point 375F. Similar to drag point 375E of FIG. 3E, drag point 375F can be used to control a zoom operation. For example, the position of drag point 375F relative to boundary 372 can yield a zoom magnitude equal to the quotient of y1 and (y1+y2) multiplied by a maximum magnification as y1 is the greatest horizontal or vertical distance between drag point 375F and boundary 372. Similarly, drag point 375F can also be used to calculate a zoom direction and distance where x1, x2, y1, and y2 are used to center electronic image 371 on drag point 375F.

Figure 4A:
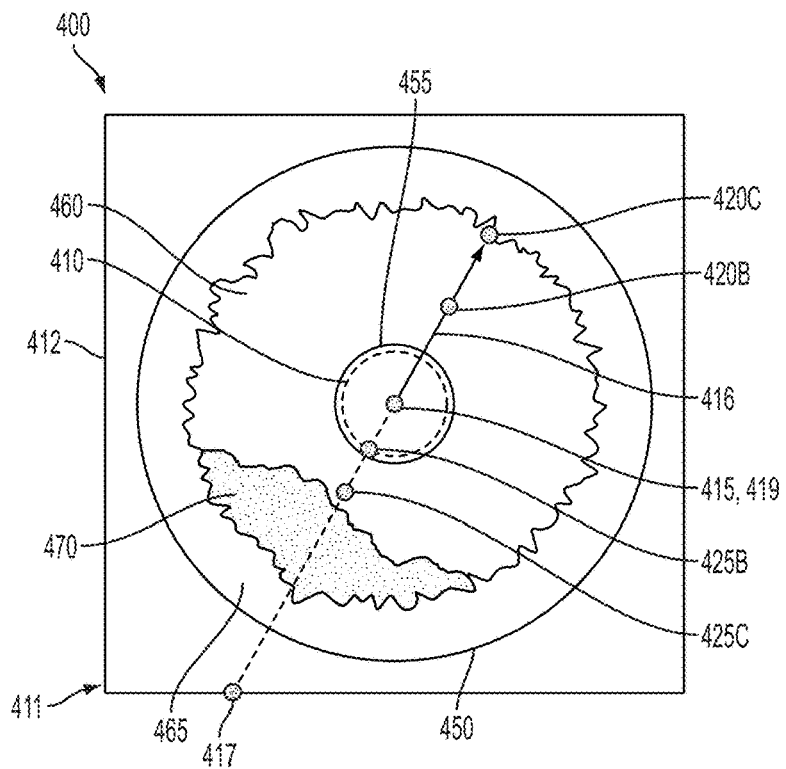
FIGS. 4A-4C are illustrative examples of an image display region of a user interface including an electronic image.
Figure 4B:
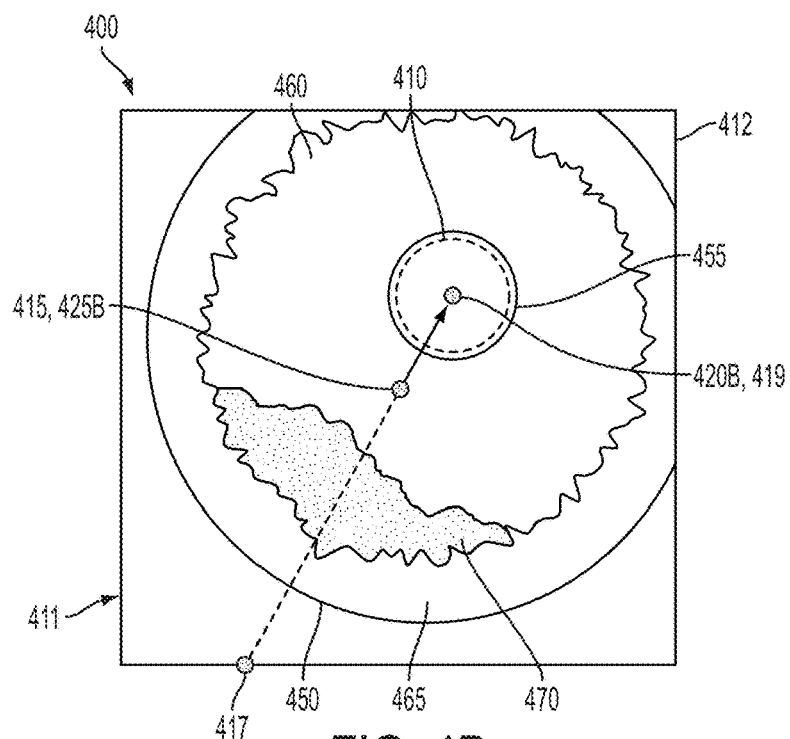
Figure 4C:
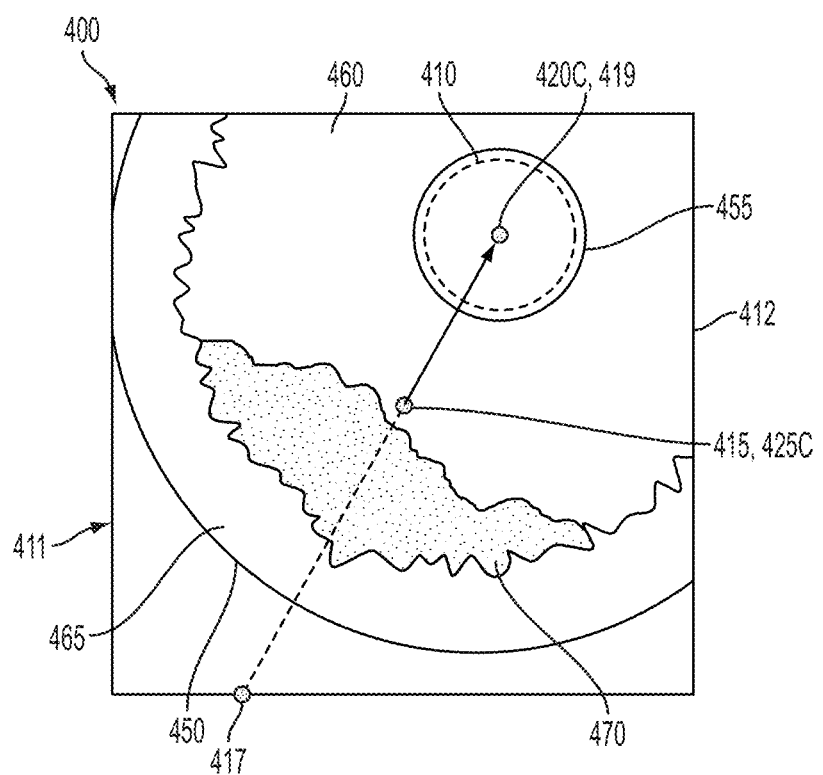

FIGS. 4A-4C are illustrative examples of an image display region 400 of a user interface including an electronic image 411. The sequence of FIGS. 4A, 4B, and 4C chronologically illustrates a method for detecting a single motion input and controlling a zoom operation on electronic image 411 based on the single motion input coinciding with a time A, a time B, and a time C, respectively. Image display region 400 may be configured to receive a single motion input from a user and control a zoom operation on electronic image 411 based on the single motion input. In this example, image display region 400 includes a context area 410, a boundary 412, a boundary point 417, the electronic image 411 and a single motion input comprising an engage point 415 and drag points 420B and 420C. Electronic image 411 may comprise a short view cross-section of a vessel 450 of a patient rendered by an imaging engine with data generated by an intravascular imaging device. Electronic image 411 may show a focal point with a catheter mask 455 encompassing the center 419 of the image, a vessel lumen 460, a vessel wall 465, and a lesion 470. Also shown in this example are zoom centers 425B and 425C which may comprise points on the electronic image that will be centered in the image display region 400 after a zoom operation is performed.

In some examples, context area 410 may be substantially the same size as, and overlay, the focal point 455 of the image. While FIG. 4A depicts the focal point of the image and the context area as positioned in the geographic center of the image, this need not be the case as the focal point could have an initial off-center position. This position of the context area 410 relative to the catheter mask may be especially advantageous for intravascular imaging applications where the area of image display region 400 enclosed by the catheter mask is substantially devoid of image data and provides a focal point around which a user may want to perform a zoom operation. In this example, the context area 410 may be substantially transparent. In certain examples where a focal point of the electronic image includes image data, it may be advantageous for the context area 410 to be substantially transparent, or translucent, so that the imaging data within the focal point may be visible to the user. In other examples, as will be discussed further below, the context area may be visible or include a zoom indicia to indicate to the user the location of the context area and/or communicate to a user how a single touch zoom operation may be performed on the user interface.

FIG. 4A illustrates image display region 400 at time A before the controlled zoom operation is performed. In this example, the image display region 400 has detected an engage point 415 within context area 410. The engage point may be representative of an input on a touchscreen from a fingertip or stylus, or a pressing of a mouse button. FIG. 4A also shows the path 416 of single motion input from time A, to time B, to time C. Drag point 420B and 420C are indicative of the positions of an input relative to the image display region 400 at time B and time C, respectively. Although depicted as such, a drag operation need not be linear; it may include curved, erratic, and/or circuitous pathways. Similarly, zoom center 425B and 425C are indicative of the zoom center of electronic image 411 at time B and time C, respectively. Note that in FIGS. 4A-C engage point 415 is depicted in relation to the user interface, not the underlying image.

As noted above, the single motion input may be used to determine a new zoom center of a zoom operation. Each zoom center may comprise a displacement distance and a displacement direction from the focal point of the electronic image. In some examples, the displacement direction may be in a substantially opposite direction from the focal point (e.g., center) of the electronic image as a direction the drag point is displaced from the engage point. For example, as shown in FIG. 4A, zoom center 425B is displaced in a substantially opposite direction from a center 419 of the electronic image as a direction the drag point 420B is displaced from engage point 415. Zoom center 425C is similarly displaced from the center 419 in a substantially opposite direction from center 419 as a direction the drag point 420C is displaced. In such embodiments, the drag operation of the user expands and centers an area of interest and pushes away from the center areas that are not of interest. In some examples, such areas not of interest can be pushed out of the boundary such that they are no longer viewable to the user. In other examples, the displacement direction may be in a substantially similar direction from the center of the electronic image as a direction the drag point is displaced from the engage point.

In some examples, the displacement distance of a zoom center may be correlated with a distance between the drag point and the boundary. In some examples, the displacement distance may be equal to a distance between the drag point and the engage point divided by a magnification limit. In this example, the magnification limit may be two, thus the distance between zoom center 425B and focal point (e.g., center 419) may be half the distance between drag point 420B and engage point 415. Similarly, the distance between zoom center 425C and center 419 may be half the distance between drag point 420C and engage point 415.

FIG. 4B shows image display region 400 at time B after a drag motion has been performed. In this example, the input has been dragged from engage point 415 to 420B. As shown in FIG. 4B, the user interface adjusts the location of the context area 410 with respect to boundary 412 based on the single motion input. Boundary point 417 may be a point on the boundary 412 that is aligned with engage point 415 and drag point 420B. In some examples, boundary point 417 may be the point on the boundary 412 such that engage point 415 is between boundary point 417 and drag point 420B.

In this example, the user interface performs a zoom operation with a zoom magnitude based on the engage point 415, drag point 420B, and boundary point 417 using similar methods as described above with respect to FIGS. 3A-3B. It should be noted that in this example, the size of context area 410 is increased to correspond with the magnification of the electronic image 411 so that the context area 410 is still substantially the same size as the focal point (e.g., catheter mask), which has undergone magnification. The user interface is also configured to center electronic image 411 not around the center 419 of the electronic image, but around zoom center 425B. Accordingly, electronic image 411 is translated such that zoom center 425B is at the center of image display region 400.

FIG. 4C shows image display region 400 at time C after a continuation of the drag motion is performed. In this example, the input has been dragged from engage point 415 to 420C. In this example the user interface again performs a zoom operation with a zoom magnitude calculated based on the engage point 415, drag point 420C, and boundary point 417.

The location of context area 410 is again adjusted with respect to boundary 412 based on the single motion input, and the size of the context area 410 is again increased to correspond with the magnification of the electronic image. Because the distance of the single motion input has increased from 420B to 420C, the zoom center has been further displaced from the center 419 of the electronic image and is now positioned at 425C. (See FIG. 4A). Accordingly, the user interface centers the electronic image 411 within image display region 400 around new zoom center 425C, instead of 425B, by translating the electronic image 411 such that zoom center 425C is at the center of image display region 400.

Figure 5:
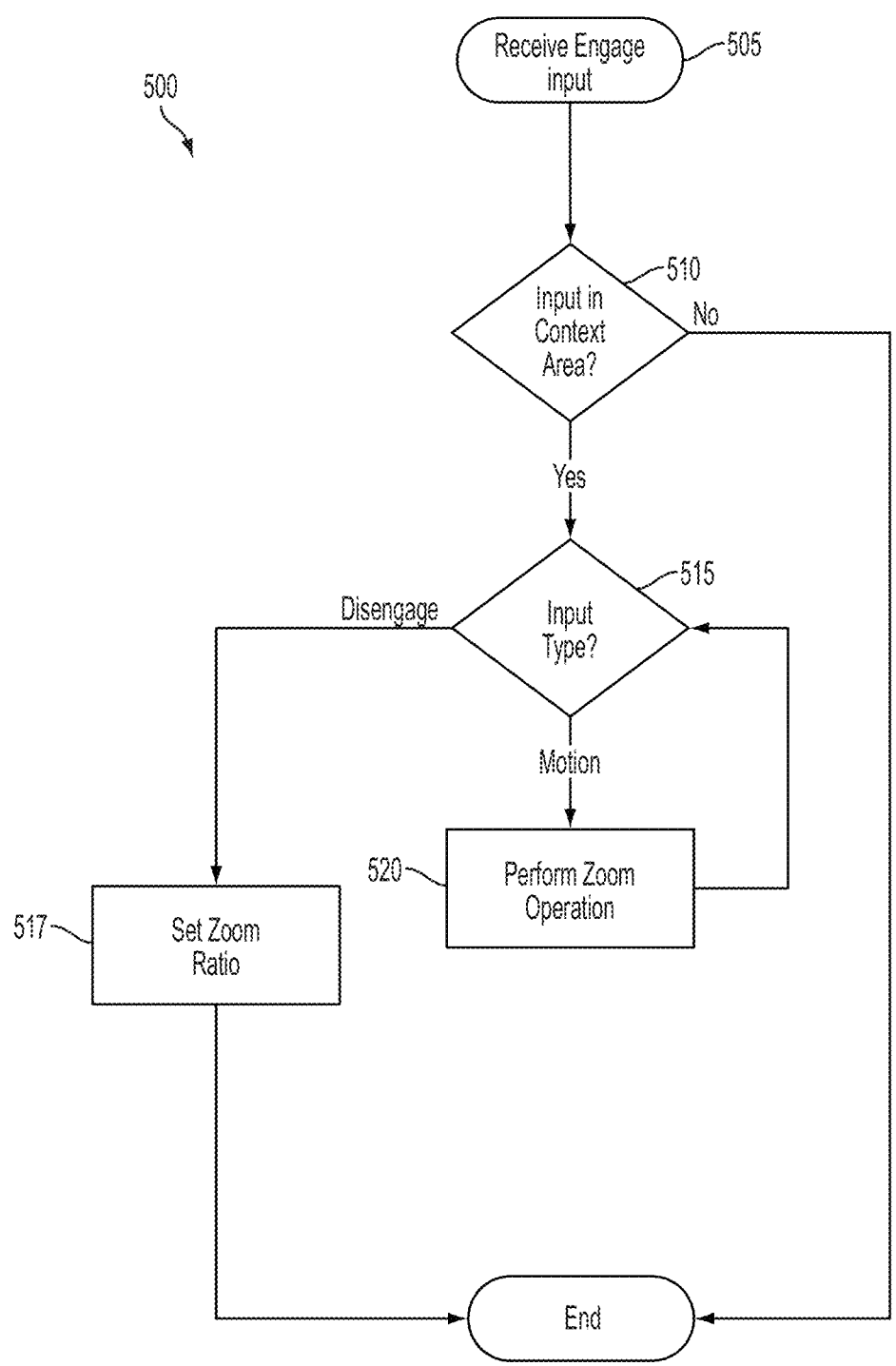
FIG. 5 is a flow diagram illustrating a method for controlling a zoom operation.

FIG. 5 is a flow diagram illustrating a method 500 for controlling a zoom operation. Method 500 provides steps to detect a single motion input and perform a zoom operation based on the single motion input. In this example, a single motion input comprises an engage input and a motion input. The single motion input continues until a disengage input is detected. In examples where a user interface is configured to receive inputs using a touch screen, an engage input, a motion input, and a disengage input may comprise an input on a touchscreen from a fingertip or stylus, a dragging of the fingertip or stylus across the surface of the touchscreen, and a removal of the fingertip or stylus from the surface of the touchscreen, respectively. Similarly, in examples where a user interface is configured to receive inputs using a mouse, an engage input, a motion input, and a disengage input may comprise a pressing of a mouse button, a dragging of a mouse while the mouse button is pressed, and a releasing of the mouse button, respectively.

A user interface configured to perform the steps of method 500 may first receive an engage input 505 from a user. The user interface may then determine in step 510 if the engage input is within a context area to determine whether the engage input was meant to initiate a zoom operation. If the input is outside of the context area, then the input is ignored for purposes of a zoom operation and the method 500 ends. If, however, the input is within the context area, then the user interface determines that a user is attempting to initiate a zoom operation and continues to step 515 where it waits for a subsequent input from the user and determines whether the subsequent input is a motion input or a disengage input.

If the user interface detects in step 515 that the next input is a motion input, then the user interface detects a single motion input and contemporaneously performs a zoom operation 520 corresponding to the motion received. The zoom operation performed in step 520 may be similar to the zoom operation described above with respect to FIGS. 4A-4C, including zooming in or out, and centering an electronic image within an image display region. After the zoom operation is performed in step 520, method 500 returns to step 515 where the user interface again determines the input type of the next input. Therefore, as long as the user interface continues to receive motion inputs from the user (e.g., the user continues to drag a finger along the surface of the touchscreen), the user interface will continue to perform zoom operations. Once a disengage input is received in step 515, however, the user interface detects a termination of the single motion input and in step 517 either continues to display the electronic image at the second magnification with the new zoom center of the electronic image centered in the image display region or automatically resets the electronic image within the image display region by setting the zoom ratio to one, according to the embodiment.

In some embodiments, a maximum zoom will be reached when the context area reaches the boundary. In such embodiments, no additional magnification is available. In certain embodiments, the zoom operation is terminated when the context area reaches the boundary and any further dragging of the context area results in a translation of the image at the maximum magnification. In such embodiments, the image can be reset to an initial zoom and position (e.g., 1x magnification and centered) by touching the context area for more than a reset duration or by any other suitable method. In other embodiments, further dragging of the context area away from the boundary continues the zoom operation.

Figure 6:
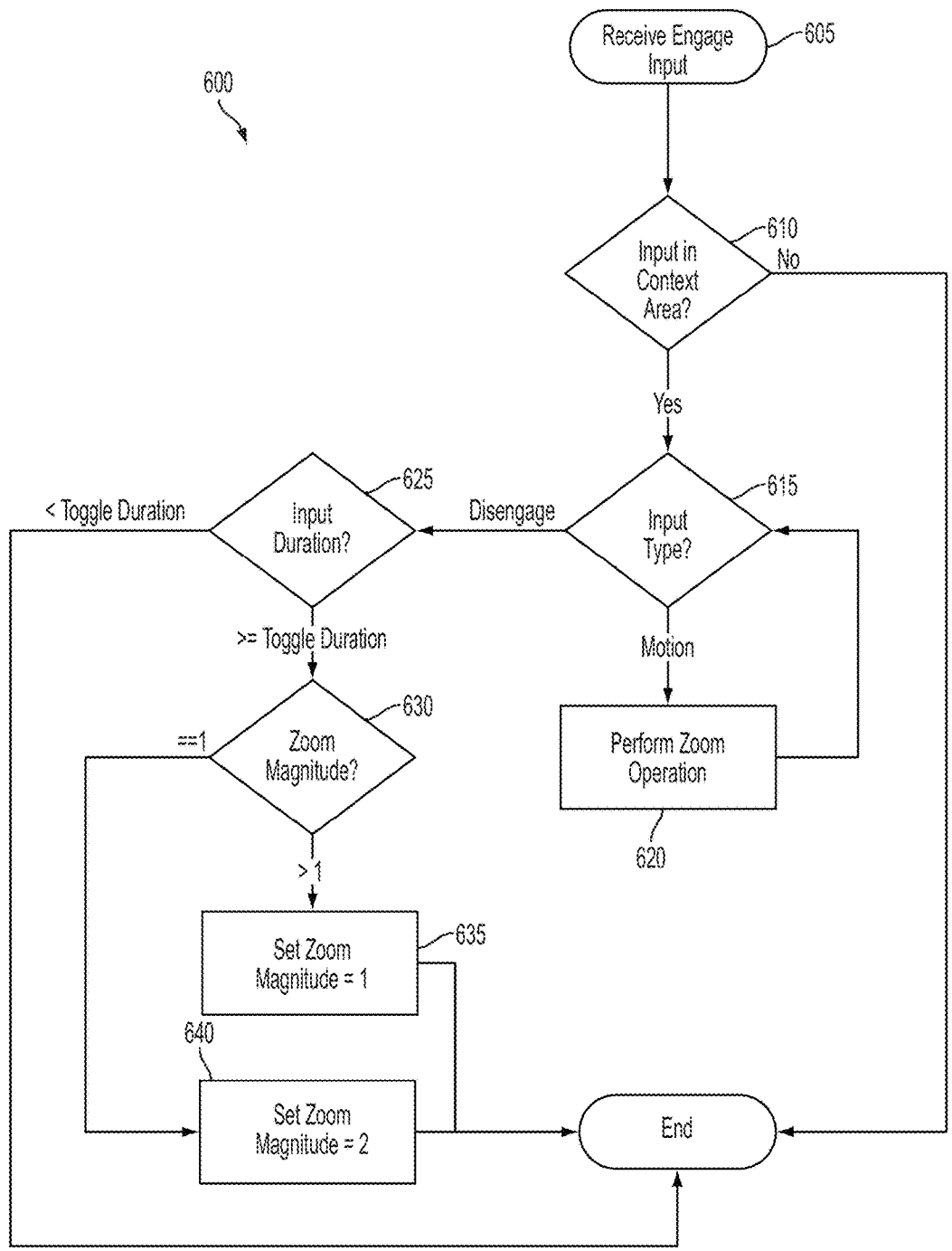
FIG. 6 is a flow diagram illustrating a method for controlling a zoom operation and for performing a toggle operation.

FIG. 6 is a flow diagram illustrating a method 600 for controlling a zoom operation. Method 600 is similar to method 500 except that it is also adapted to receive a toggle operation from a user. A toggle operation may simply change the zoom magnitude to either one or a magnification limit depending on a current zoom magnification. In some examples, if a current zoom magnitude is currently one (e.g., no zoom operation is performed), a toggle operation will set the zoom magnification to a magnification limit. If, however, the current zoom magnitude is not equal to one (e.g., a zoom operation has been performed), then the toggle operation will set the zoom magnification back to one. In some examples, a toggle operation may comprise an engage input and a disengage input without detecting a motion input. For example, a toggle input may be detected when a user touches a touchscreen with a fingertip or a stylus within a context area for a period of time without moving the fingertip or the stylus. It can be appreciated that inadvertent movements are likely to occur even when a user intends to perform a toggle operation. Thus, while not explicitly represented in method 600, error bounds may be incorporated into implementations of method 600.

Similar to method 500, a user interface configured to perform the steps of method 600 may first receive an engage input 605 from a user and determine whether the engage input is within a context area in step 610. If the input is outside the context area, then the input is ignored and the method 600 ends. If, however, the input is within the context area, then the user interface waits for a subsequent input from the user. At this point, method 600 deviates from method 500 in that a toggle operation may be performed based on the next input received.

A toggle operation is performed if the next input type received from the user interface is determined in step 615 to be a disengage input. The user interface may then determine that the engage input received in step 605 was meant to initiate a toggle operation and not a zoom operation because the user did not provide the motion input necessary to perform a zoom operation. The user interface may then calculate an input duration in step 625 by comparing the time the engage input was received in step 605 with the time the release input was received in step 615. If the duration is longer than a toggle duration, then the user interface may perform a toggle operation in either step 635 or step 640 based on a current zoom magnitude as determined in step 630. If, however, the duration is not longer than the toggle duration, then the user may determine that engage input in the context area was inadvertent and ignore the input. In some examples, the toggle duration may between one and two seconds. If a toggle operation is not detected in step 615 (i.e., a motion input was detected), then method 600 continues on, as in method 500, where the user interface continues to perform zoom operations in step 620 so long as motion inputs are detected in step 615.

Figure 7:
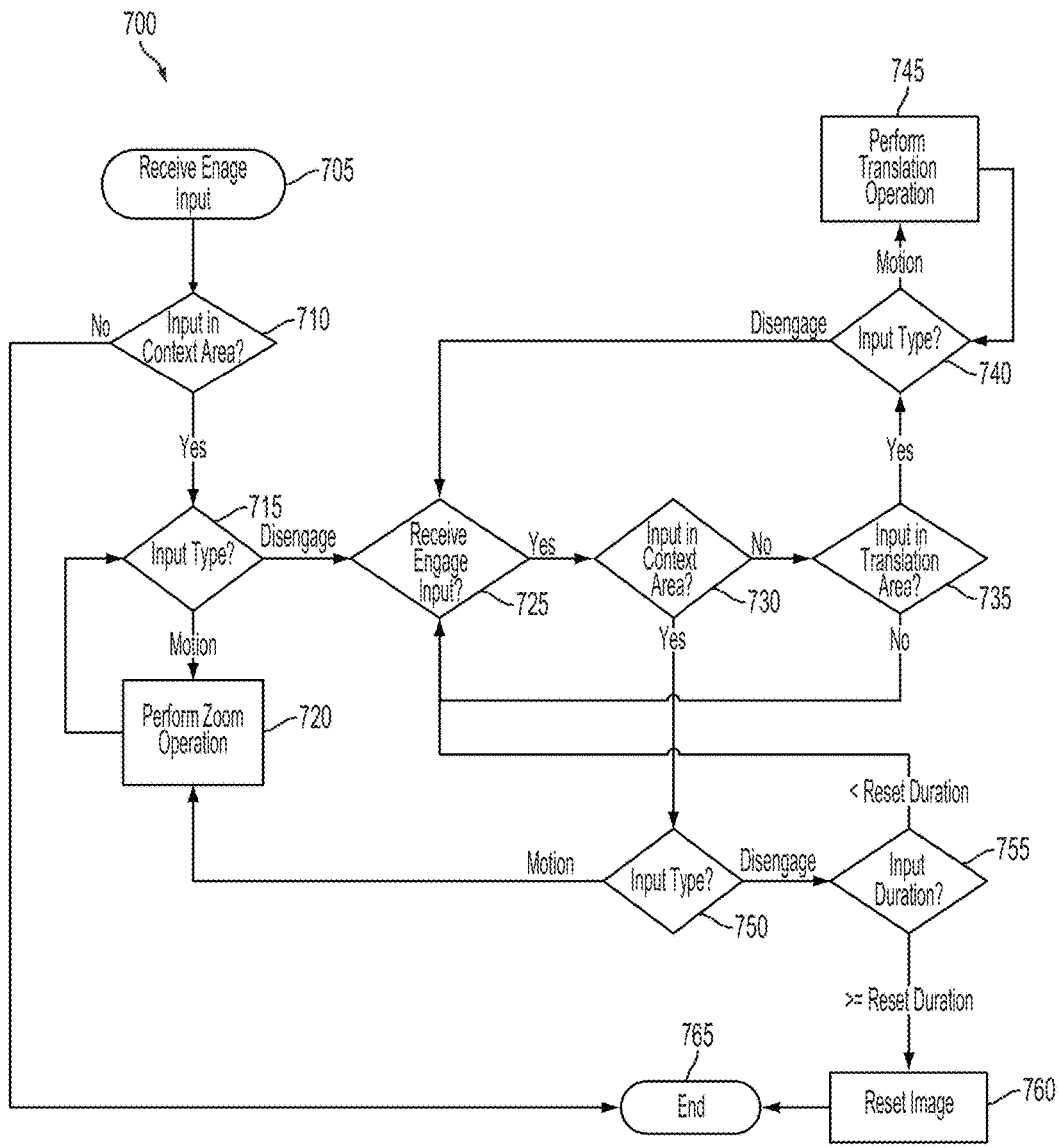
FIG. 7 is a flow diagram illustrating a method for controlling a zoom operation and a translation operation.

FIG. 7 is a flow diagram illustrating a method 700 for controlling a zoom operation. In some examples, an image display region may include a defined translation area in addition to a defined context area. In some examples, the translation area may be distinct from the context area. In certain examples, the translation area may comprise all of the remaining area of an image display region outside of the context area. Method 700 allows a user to perform a zoom operation with a single motion input to identify an area of interest then adjust the viewing of the area of interest using another single motion input to translate the image with the image display region. This method provides the advantage of allowing a user to fine tune the area of an electronic image viewed without having to perform another zoom operation.

Similar to method 500, a user interface configured to perform the steps of method 700 may first receive an engage input in step 705 from a user and determine whether the engage input is within a context area in step 710. If the input is outside the context area, then the user input is ignored for purposes of zoom and method 700 ends. If, however, the input is within the context area, then the user interface waits for a subsequent input from the user. If the user interface detects a motion input in step 715, then the user interface continues to perform zoom operations in step 720 so long as motion inputs are detected in step 715.

Once a disengage input is received in step 715, the user interface detects a termination of the single motion input, proceeds to step 725, and takes no action until another engage input is received. Thus, after a zoom operation is completed by a user, the user interface keeps the zoom settings and awaits further action from the user. This may be especially advantageous for user interfaces including a touchscreen as it allows the user to remove their finger from the image display area and more closely examine the electronic image.

At this point in method 700, a user has the option of performing a translation operation, performing another zoom operation, or providing a reset input to set the zoom magnitude back to one. A translation operation may be initiated by the user by providing an engage input within the translation area of the image display region. In such an example, the engage input will be received in step 725 and determined to be within the translation area in step 735. Upon receiving a subsequent motion input in step 740, the user interface detects a single motion input comprising the engage input received in step 725 and the motion input received in step 740. The user interface then continuously performs a translation operation by alternating between steps 740 and 745 until a disengage input is received in step 740. Upon termination of the single motion input, the user interface returns to step 725 where it again waits for an engage input from the user.

The user may also initiate another zoom operation by providing an engage input within the context area of the image display region. In such an example, the engage input will be received in step 725 and determined to be within the context area in step 730. If the user interface receives a subsequent motion input in step 750, the user interface detects a single motion input comprising the engage input received in step 725 and the motion input received in step 750. The user interface then continuously performs a zooming operation by again alternating between steps 715 and 720 until a disengage input is received in step 715. After termination of the single motion input, the user interface returns to step 725 where it again waits for an engage input from the user.

After a user is finished inspecting the electronic image at the selected zoom magnitude, the user may initiate a reset of the electronic image by providing an engage input in the context area and a disengage input without a motion input. The engage input will be received in step 725 and determined to be within the context area in step 730. Once the user interface receives the disengage input in step 750, the user interface will calculate a duration between the engage input received in step 725 and the disengage input received in step 750. If the duration of the input is less than a reset duration, then the user interface ignores the input as an inadvertent input. If, however, the duration of the input is greater than or equal to the reset duration, the user interface resets the image in step 760 and ends method 700. In some examples, the reset duration may be between 0.1 and 1 second. The method of FIG. 7 can be combined with the method of FIG. 6 and include toggling functions.

Figure 8A:
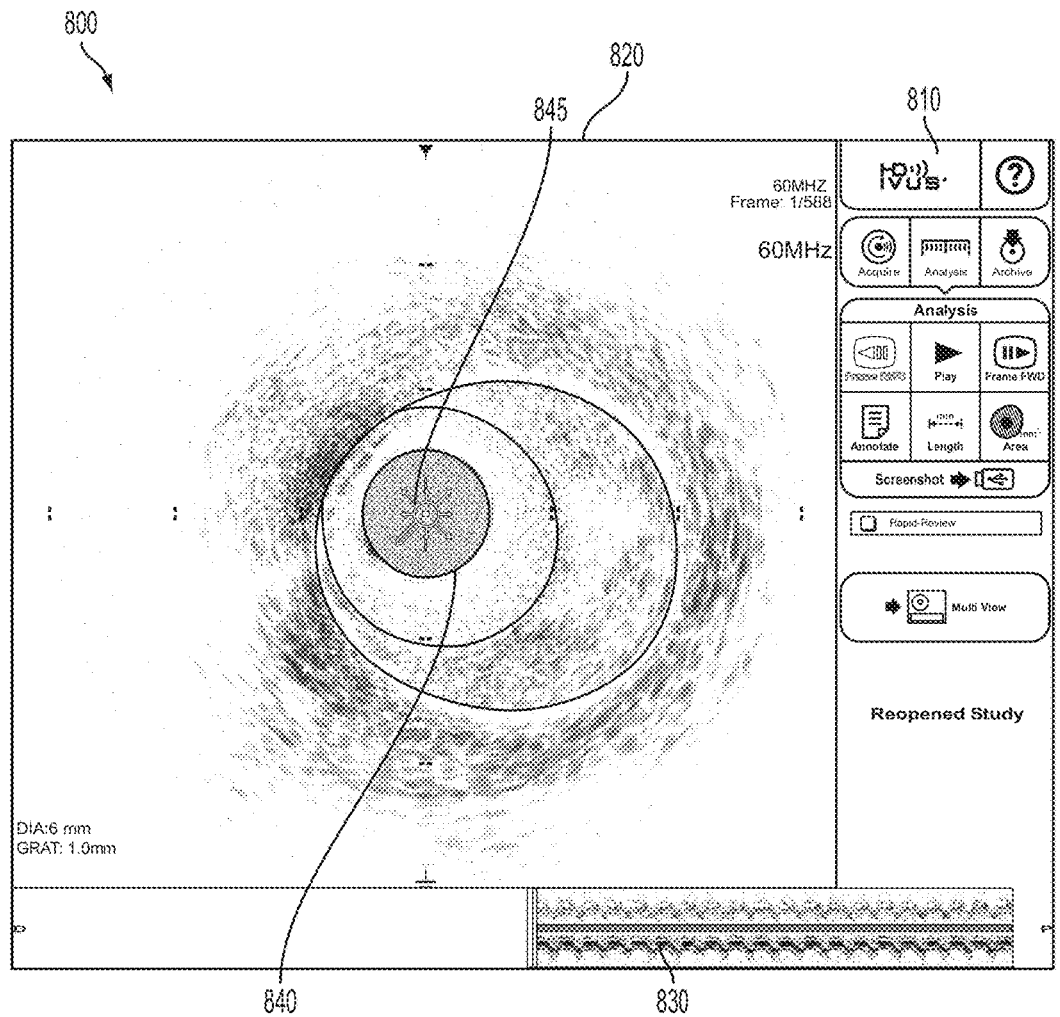
FIGS. 8A-8F show a user interface for controlling a zoom operation.

FIGS. 8A-8F show examples of user interface 800 for controlling a zoom operation. FIG. 8A shows a user interface 800 including a menu 810, an image display region 820, and a data display area 830. In this example image display region 820 shows a short view cross-section image of a vessel while the data display region shows a long view cross-section image of the vessel. The image display region 820 includes a catheter mask. A context area 840 overlays the catheter mask and is marked with a zoom indicia 845 to help indicate to a user the position of the context area 840 with the image display region 820. As shown in FIG. 8A, an embodiment of a zoom indicia can include a magnifying glass overlaid with one or more arrows. The magnifying glass is provided to inform a user that selecting the zoom indicia, thereby selecting the context area 840, will allow the user to perform a zoom operation. The arrows are provided to inform a user that a zoom operation may be performed by selecting and moving the magnifying glass. In some examples, the zoom indicia may be configured to show only a magnifying glass until the context area 840 is selected, after which the magnifying glass may be removed and replaced with one or more arrows to indicate to the user to move the context area 840.

Figure 8B:
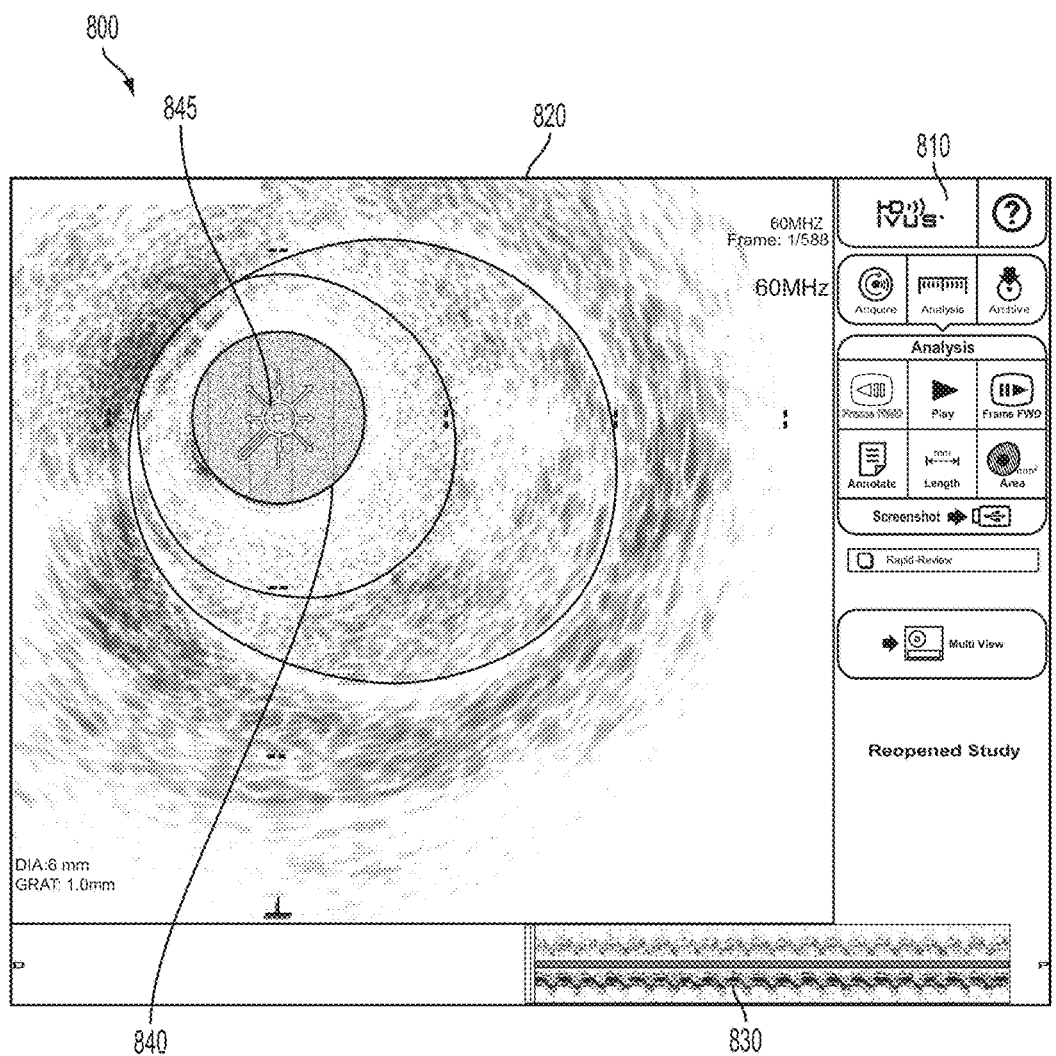
Figure 8C:
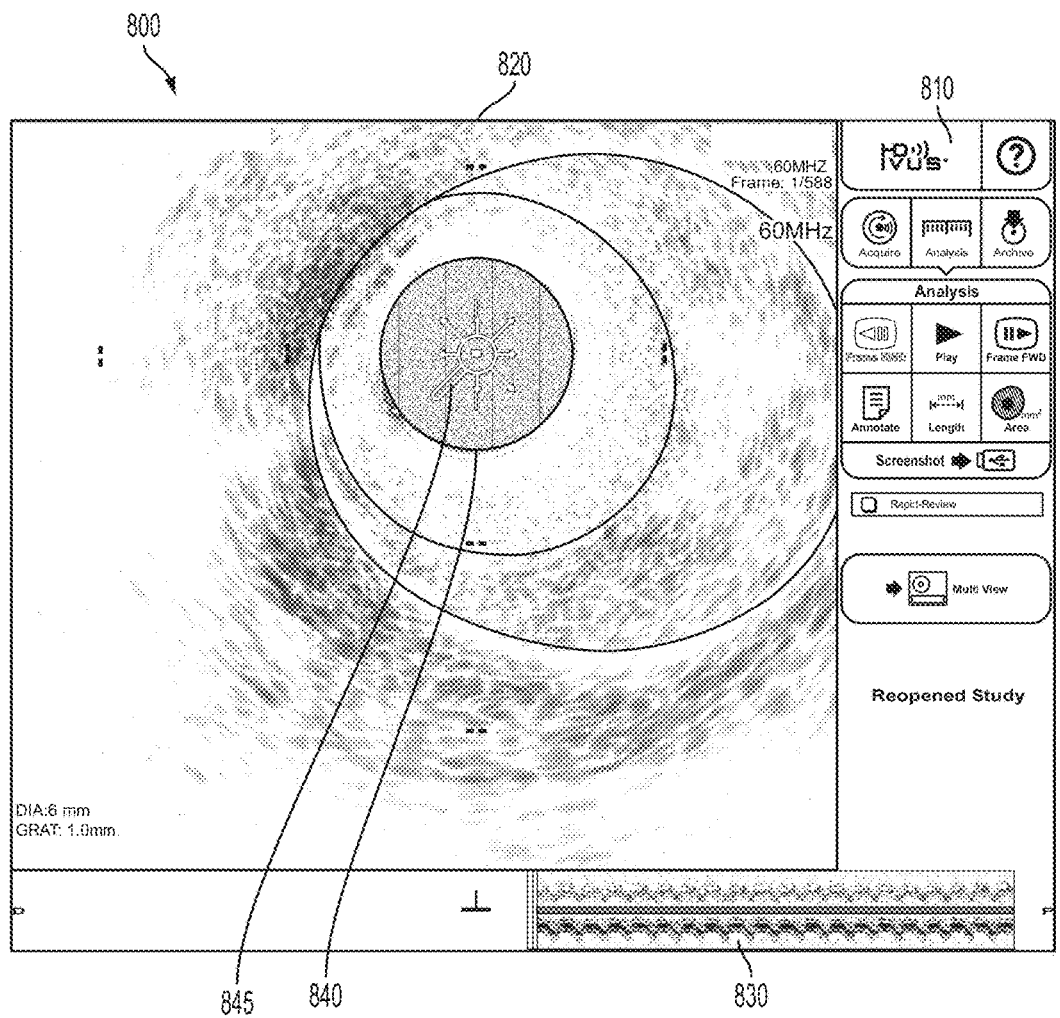
Figure 8D:
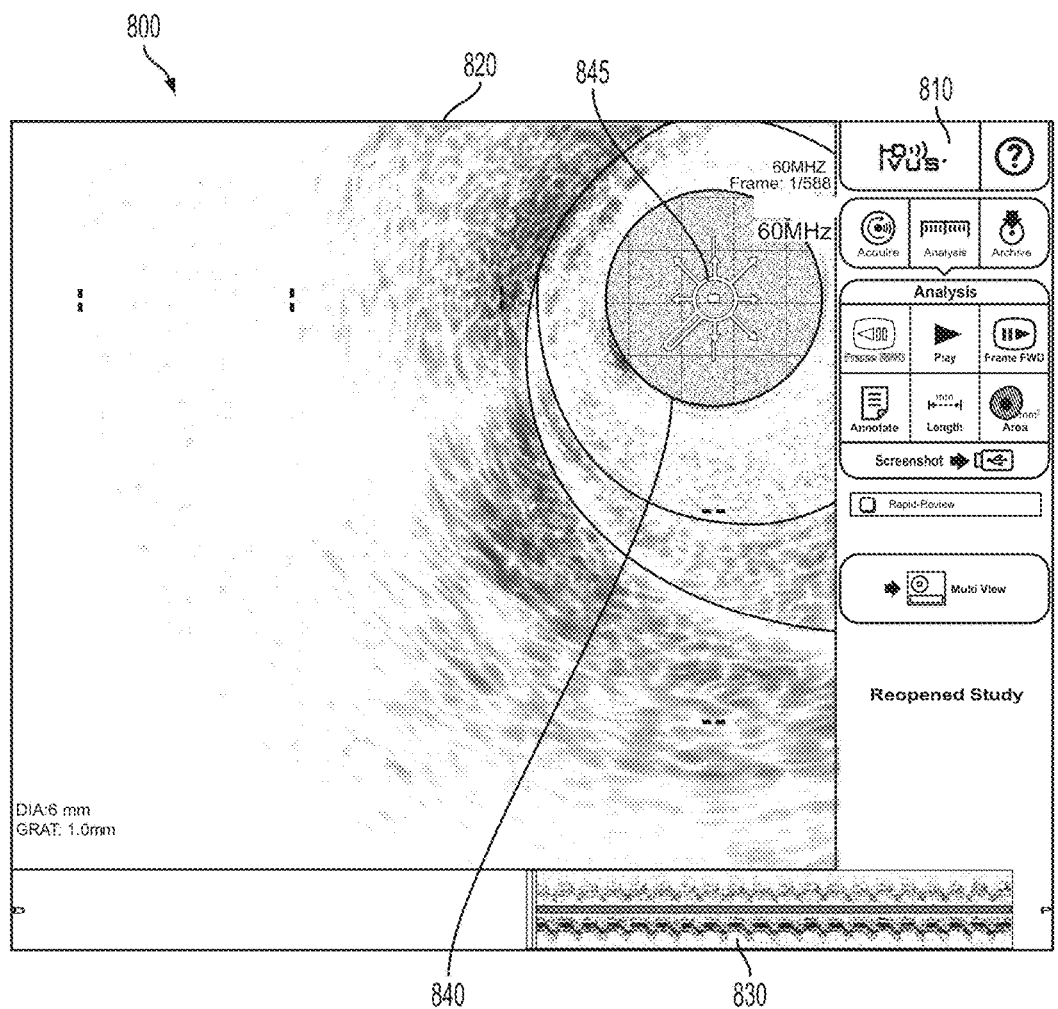
Figure 8E:
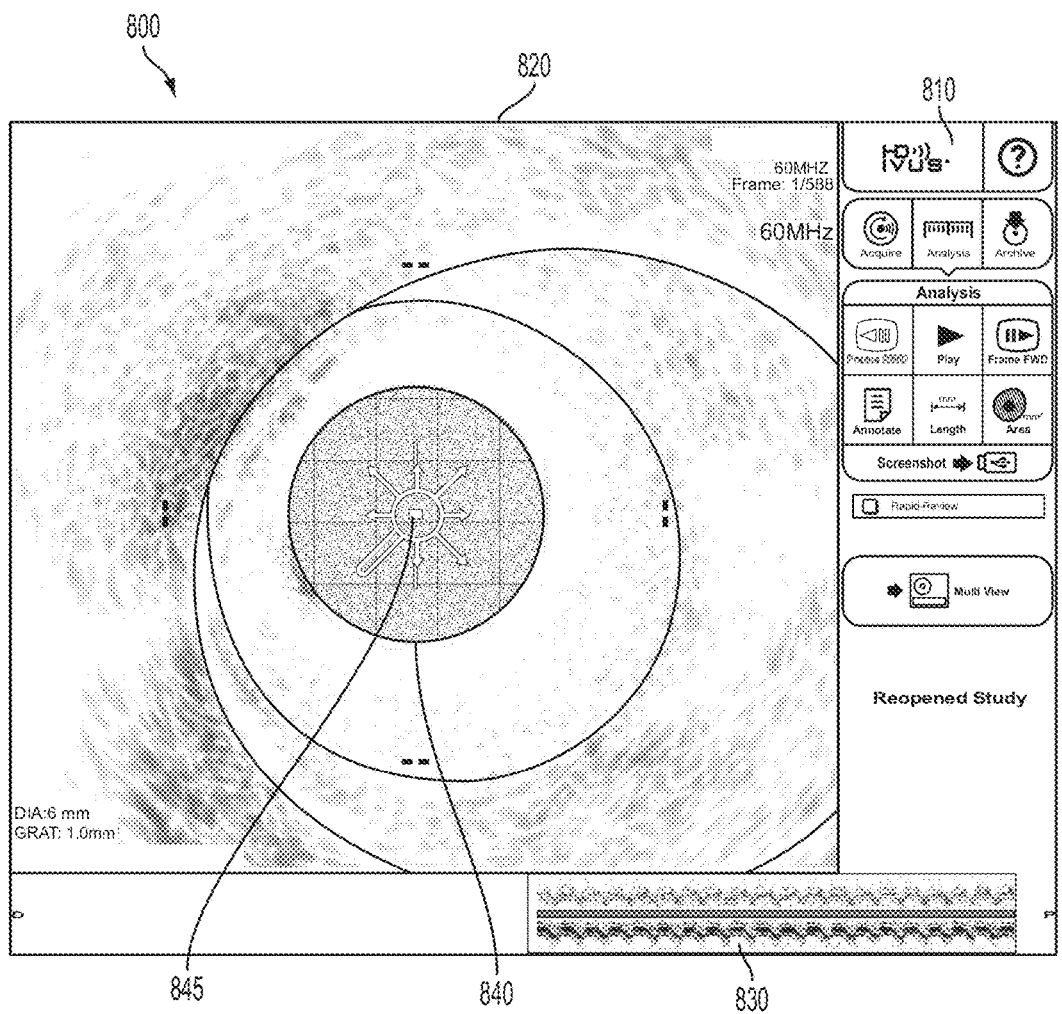
Figure 8F:
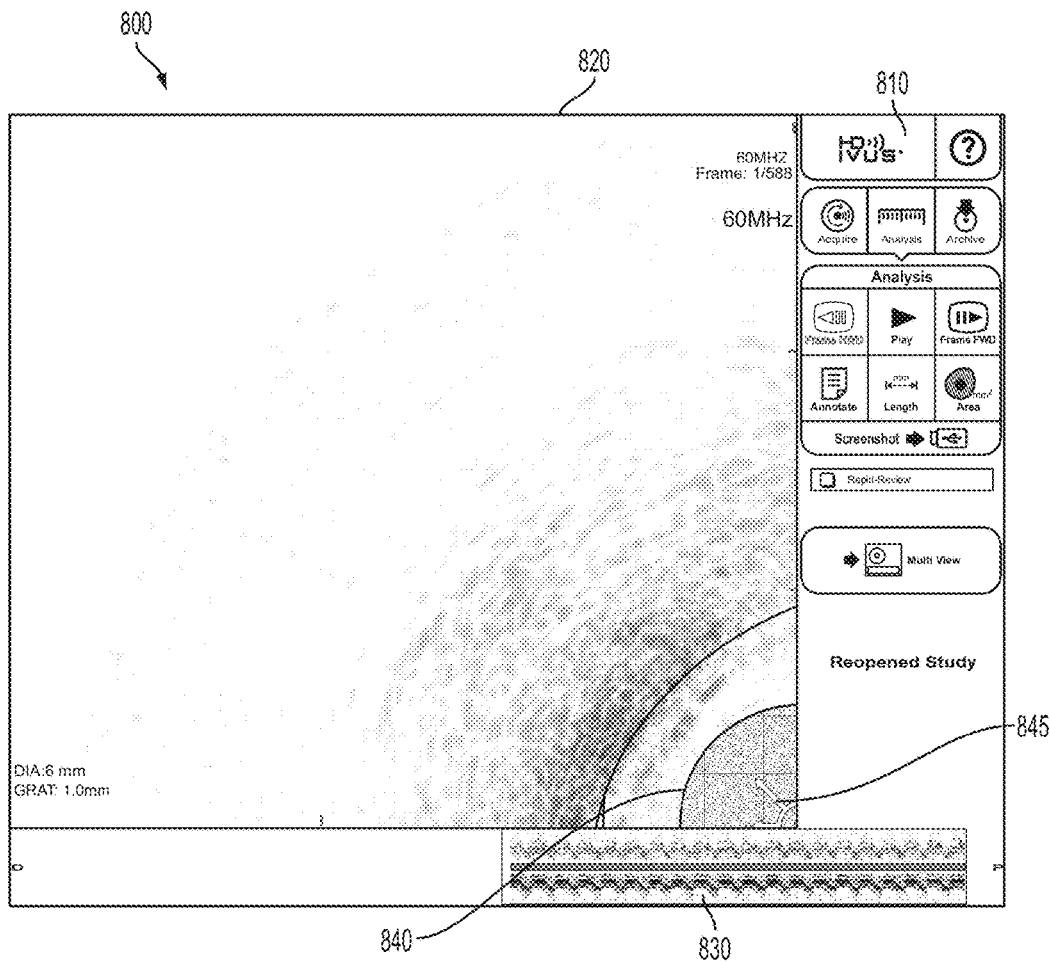

FIG. 8A shows the context area 840 at the center of the image display region 820 before a zoom operation is performed. FIG. 8B shows the context area 840 moved to the upper left hand corner of the image display region 820 causing the user interface to perform a zoom operation by zooming in and centering the electronic image on a zoom center displaced down and to the right of the electronic image center. FIG. 8C shows the context area 840 moved slightly to the right to view a different portion of the electronic image. FIG. 8D shows the context dragged slightly to the right again to view a different portion of the electronic image. FIG. 8E shows the result of a toggle operation causing the user interface to change the zoom magnitude to the magnification limit centered around the catheter mask. FIG. 8F shows a the context dragged to the right hand corner of the image display region 820 causing the user interface to zoom in at the magnification limit with a zoom center displaced near the upper left hand corner of the electronic image.

Various examples of the invention have been described. Although the present invention has been described in considerable detail with reference to certain disclosed embodiments, the embodiments are presented for purposes of illustration and not limitation. Other embodiments incorporating the invention are possible. One skilled in the art will appreciate that various changes, adaptations, and modifications may be made without departing from the spirit of the invention and the scope of the appended claims.

What is claimed is:

1. A device comprising:
    a user interface including an image display region for displaying an electronic image, the image display region having a boundary and a defined context area within the boundary, the user interface configured to receive user inputs from a user; and
    an imaging engine including one or more processors and memory, the imaging engine configured to:
        display the electronic image within the image display region of the user interface at a first zoom magnification;
        detect a single motion input from the user to adjust the location of the context area with respect to the boundary, the single motion input comprising:
            an engage input at an engage point within the context area;
            a disengage input at a drag point; and
            a drag input beginning at the engage point, extending towards the boundary of the user interface, and ending at the drag point; and
        control a zoom operation on the electronic image contemporaneously with and corresponding to the detected single motion input, the zoom operation including:
            calculating, based on the single motion input, a new zoom center of the electronic image and a second zoom magnification, wherein the new zoom center comprises a displacement direction and a displacement distance from a focal point of the electronic image, and wherein the displacement distance is equal to a distance between the drag point and the engage point divided by a magnification limit; and
            displaying the electronic image at the second zoom magnification with the new zoom center of the electronic image centered in the image display region.

2. The device of claim 1, wherein the second zoom magnification is equal to a quotient of (
    a) a distance between the drag point and a boundary point, the boundary point being aligned with both the drag point and the engage point such that the engage point is between the drag point and the boundary point, and
    (b) a distance between the engage point and the boundary point.

3. The device of claim 1, wherein the second zoom magnification is correlated with a quotient of
    (a) a distance between the drag point and the boundary of the image display region, and
    (b) a dimension of the boundary of the image display region.

4. The device of claim 3, wherein the dimensions of the boundary of the image display region and the distance between the drag point and the boundary are calculated based on a coordinate system.

5. The device of claim 3, wherein the distance between the drag point and the boundary is the greatest horizontal distance or vertical distance between the drag point and the boundary.

6. The device of claim 1, wherein the second zoom magnification is equal to multiplying the magnification limit with a quotient of
    (a) a distance between the drag point and the engage point, and
    (b) a distance between the engage point and a boundary point, the boundary point being aligned with both the drag point and the engage point such that the drag point is between the engage point and the boundary point.

7. The device of claim 6, wherein the magnification limit is 2.

8. The device of claim 1, wherein the displacement direction is in an opposite direction from the center of the electronic image as the drag point is displaced from the engage point.

9. The device of claim 1, wherein the displacement direction is in a similar direction from the center of the electronic image as the drag point is displaced from the engage point.

10. The device of claim 1, wherein the device further comprises a mouse, the user interface is configured to receive user inputs from a user via the mouse, the engage input is a press of a button of the mouse, and the disengage input is a release of the button of the mouse.

11. The device of claim 1, wherein the device further comprises a touchscreen, the engage input is a touch on the touchscreen, and the disengage input is a removal of the object from the touchscreen.

12. The device of claim 11, wherein the touchscreen comprises a surface acoustic wave touchscreen.

13. The device of claim 1, wherein in response to the disengage input, the imaging engine is to continue to display the electronic image at the second zoom magnification with the new zoom center of the electronic image centered in the image display region.

14. The device of claim 1, wherein in response to the disengage input the imaging engine is to automatically reset the electronic image in the image display region.

15. The device of claim 1, wherein the imaging engine is configured to detect a reset input from the user.

16. The device of claim 13, wherein the reset input is detected by an intersection of the context area and the boundary.

17. The device of claim 13, wherein the reset input is detected by the imaging engine when a user engages the context area without moving with respect to the engage point, for more than a reset duration.

18. The device of claim 1, wherein the imaging engine is configured to detect a zoom toggle input from the user and display the image at the first zoom magnification if a current zoom magnification is not equal to the first zoom magnification, or display the image at a maximum zoom magnification if the current zoom magnification is equal to the first zoom magnification.

19. The device of claim 18, wherein the toggle input is detected by the imaging engine when a user engages the context area without moving with respect to the engage point, for more than a toggle duration.

20. The device of claim 1,
wherein the user interface comprises a defined translation area within the boundary and the imaging engine is configured to detect a translation motion input from the user, the translation motion input:
beginning at a translation engage point within the translation area,
extending towards the boundary of the user interface, and
ending at a translation drag point; and
wherein the imaging engine is configured to translate the electronic image within the image display region a translation distance and translation direction directly correlated with a distance between the translation engage point and the translation drag point and a direction from the engage point to the drag point.

21. The device of claim 20, wherein the translation area is distinct from the context area.

22. The device of claim 1, wherein a size of the context area is directly correlated with a zoom magnification of the electronic image.

23. The device of claim 1, wherein the context area includes a visible zoom indicia within the context area.

24. The device of claim 1, wherein the focal point corresponds with an area of the electronic image devoid of image data.

25. The device of claim 24, wherein the context area is overlaid with the focal point.

26. The device of claim 25, wherein the imaging engine is further configured to receive an input from the user to overlay the context area with the focal point of the electronic image.

27. The device of claim 25, wherein the imaging engine is further configured to automatically identify the focal point of the electronic image and overlay the context area with the focal point.

28. The device of claim 1, wherein the device is a computing device of an intravascular imaging system.

29. A system comprising:
a catheter assembly including an intravascular imaging device having an imaging module configured to emit and receive energy and generate imaging data;
a user interface including an image display region, the image display region having a boundary and a defined context area within the boundary, the context area corresponding to a catheter mask within a vessel of a patient, the user interface configured to receive user inputs from a user; and
an imaging engine in communication with the intravascular measuring device and the user interface, the imaging engine being adapted to:
generate an electronic image including a cross-section of the vessel based on the imaging data;
display the electronic image within the image display region of the user interface at a first zoom magnification;
detect a single motion input from the user to adjust the location of the context area with respect to the boundary, the single motion input comprising:
an engage input at an engage point within the context area;
a disengage input at a drag point; and
a drag input beginning at the engage point, extending towards the boundary of the user interface, and ending at the drag point; and
control a zoom operation on the electronic image contemporaneously with and corresponding to the detected single motion input, the zoom operation including:
calculating, based on the single motion input, a new zoom center of the electronic image and a second zoom magnification, wherein the new zoom center comprises a displacement direction and a displacement distance from a focal point of the electronic image, and wherein the displacement distance is equal to a distance between the drag point and the engage point divided by a magnification limit; and
displaying the electronic image at the second zoom magnification with the new zoom center of the electronic image centered in the image display region;
wherein the boundary of the image display region is unmodified by the zoom operation.

30. A system, comprising:
a display device having a user interface including an image display region for displaying an electronic image, the image display region having a boundary and a defined context area within the boundary, the user interface configured to receive user inputs from a user;
an imaging engine including one or more processors and memory, the memory including instructions that, when executed by the one or more processors, cause the imaging engine to:
receive imaging data and generate an electronic image based on the imaging data;
receive user inputs from a user;
display the electronic image within the image display region at a first zoom magnification;
detect a single motion input from a user, the single motion input beginning at an engage point within the context area and ending at a drag point; and
control a zoom operation on the electronic image contemporaneously with and corresponding to the detected single motion input, the zoom operation to cause the imaging engine to calculate a new zoom center of the electronic image and to cause the user interface to display the electronic image at a second zoom magnification, the zoom operation controlled as a function of the single motion input;

wherein the new zoom center comprises a displacement direction and a displacement distance from a focal point of the electronic image; and wherein the displacement distance is equal to a distance between the drag point and the engage point divided by a magnification limit; and wherein the boundary of the image display region is unmodified by the zoom operation.

31. The system of claim 29, wherein the second zoom magnification is equal to a quotient of:
 (a) a distance between the drag point and a boundary point, the boundary point being aligned with both the drag point and the engage point such that the engage point is between the drag point and the boundary point, and
 (b) a distance between the engage point and the boundary point.

32. The system of claim 30, wherein the system is an intravascular imaging system.

33. The system of claim 30, wherein the displacement direction is in an opposite direction from the focal point as a direction in which the drag point is displaced from the engage point.

* * * * *